(12) United States Patent
Bianchi et al.

(10) Patent No.: US 9,297,114 B2
(45) Date of Patent: Mar. 29, 2016

(54) PRODUCT FOR THE TREATMENT OF WASTEWATERS AND SEWAGE AND METHODS THEREFORE

(75) Inventors: Gianluca Bianchi, Borgio Verezzi (IT); Matteo Benedusi, Pietra Liagure (IT); Lorenzo Altheimer, Segrate (IT)

(73) Assignee: BBA Biotech SRL, Milan (IT)

( * ) Notice: Subject to any disclaimer, the term of this patent is extended or adjusted under 35 U.S.C. 154(b) by 2033 days.

(21) Appl. No.: 12/093,101

(22) PCT Filed: Nov. 11, 2005

(86) PCT No.: PCT/EP2005/012080
§ 371 (c)(1),
(2), (4) Date: Sep. 19, 2008

(87) PCT Pub. No.: WO2007/054114
PCT Pub. Date: May 18, 2007

(65) Prior Publication Data
US 2009/0017524 A1    Jan. 15, 2009

(51) Int. Cl.
*A61F 13/15* (2006.01)
*C02F 3/34* (2006.01)
*D21H 17/00* (2006.01)
*A61F 13/84* (2006.01)

(52) U.S. Cl.
CPC ........ *D21H 17/005* (2013.01); *A61F 13/15252* (2013.01); *A61F 13/8405* (2013.01); *C02F 3/341* (2013.01); *Y10T 428/31504* (2015.04)

(58) Field of Classification Search
CPC . A61F 13/15252; A61F 13/8405; C02F 3/34; C02F 3/341; C02F 2303/20; C02F 3/02; C02F 3/1268; C02F 3/20; D21H 17/005; C12N 1/36; C12N 15/8262; C12N 15/8279; C12P 7/6463; C12P 7/649; Y02E 50/13; A01H 3/00; C11D 3/046; C11D 3/30; C11D 3/381; C11D 3/386; C11D 17/041; C11D 3/38663; C11D 3/48; C11D 3/166; C11D 3/3707; C11D 11/0023; C11D 17/0047; C11D 1/22; C11D 1/29; C11D 1/662; C11D 3/162; C11D 3/38645; A61K 2300/00; A61K 35/742; A61K 35/74; A61K 31/496; A61K 31/4178; A61K 31/704; A61K 31/7048; A61K 35/36; A61K 35/744; A61K 35/745; A61K 35/747; A61K 47/44; A61K 9/0014; A61K 9/0034; A61K 45/06; A01N 25/00; A01N 63/00; A01N 63/02; A01C 1/00; A01C 1/06; C12R 1/07; Y10T 428/31504
See application file for complete search history.

(56) References Cited

U.S. PATENT DOCUMENTS

| | | | |
|---|---|---|---|
| 5,223,140 A * | 6/1993 | Rutherford et al. | 210/605 |
| 5,543,309 A | 8/1996 | Pischel | |
| 5,905,037 A * | 5/1999 | Cooney et al. | 435/264 |
| 2003/0008377 A1 * | 1/2003 | Lee et al. | 435/252.1 |
| 2004/0115090 A1 * | 6/2004 | Andersson et al. | 422/1 |

FOREIGN PATENT DOCUMENTS

WO    WO 00/01621 A    1/2000

OTHER PUBLICATIONS

T.S.M Pirattijärvi et al.: "Bacterial contaminants in liquid packaging boards: assessment of potential for food spoilage" Journal of Applied Bacteriology, vol. 81, 1996, pp. 445-458, XP008062345 figure 1.
D.T.W. Chun et al. : "Profile of bacterial genera associated with cotton from low endotoxin and high endotoxin growing regions" Ann. Agric. Environ. Med., vol. 4, 1997, pp. 233-242, XP002397109 p. 240; table 6.

* cited by examiner

*Primary Examiner* — Debbie K Ware
(74) *Attorney, Agent, or Firm* — Arent Fox LLP

(57) ABSTRACT

Biodegradable support carrying a mixture of non-pathogenic bacteria that synergistically cooperate in decomposing the organic pollutants present in toilet wastewaters and in sewage collection and processing tanks. Method for manufacturing a product comprising the biodegradable support having a bacterial mixture comprised of *Bacillus* species. Further, a method for degrading organic substances using the product.

8 Claims, 4 Drawing Sheets

SAMPLE A    SAMPLE B    SAMPLE C

PRODUCT FOR THE TREATMENT OF WASTEWATERS AND SEWAGE AND METHODS THEREFORE

CROSS-REFERENCE TO RELATED APPLICATION

This application is a national Stage entry of International Application No. PCT/EP2005/01080, filed Nov. 11, 2005, the entire specification claims of which are incorporated herewith by reference.

The present invention provides means for biodegrading the organic pollutants present in wastewaters and for preventing the formation of agglomerates along the sewer pipes.

More specifically, the invention provides a biodegradable solid support carrying a mixture of non-pathogenic bacteria that synergistically cooperate in decomposing the organic pollutants present in toilet wastewaters and in sewage collection and processing tanks, including the organic agglomerates which lead to blockages along sewer pipes.

BACKGROUND OF THE INVENTION

The problem of effectively degrading the organic substances contained in wastewaters and sewage has been long felt. Besides to evidently causing hygienic problems, such organic substances are also responsible for the formation of encrustations and therefore of serious damages in time, along domestic pipelines to drainpipes.

Biological and chemical products are currently used to safeguard the integrity and good state of pipelines to drainpipes; in many cases such products may result either harmful to the user or scarcely effective in eliminating the substances responsible for pipe blockage and sewage sludge accumulation.

STATE OF THE ART

The patent application WO00/01621 discloses biological means for sanitary drainage of polluted effluents and/or maintenance of a sewer pipe system for evacuating said effluents, characterised in that it comprises at least a biodegradable support, particularly bioactive toilet paper loaded with a composition of saprophytic bacteria belonging to at least one of the species *Bacillus subtilis, Rhodococcus rubica, Rhodococcus rubra, Pseudomonas putida, Pseudomonas putrefaciens*.

DISCLOSURE OF THE INVENTION

Figure 1:
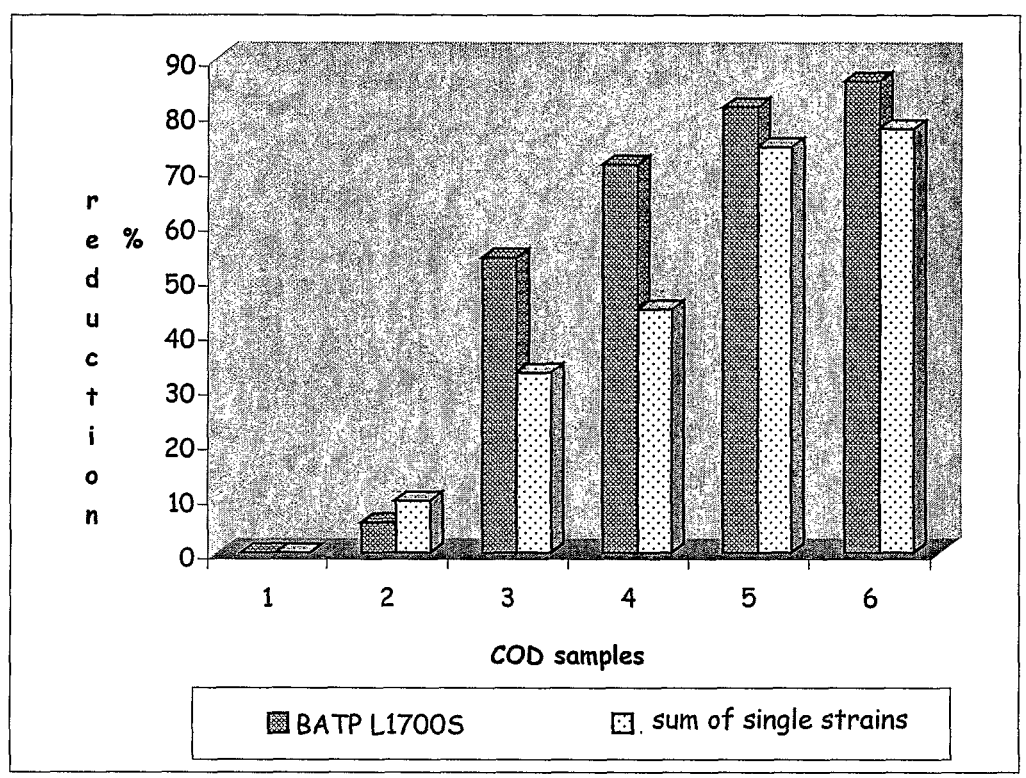
FIG. 1 is a graph showing the total percentage reduction in pollutant content of five bacterial strains (*Bacillus subtilis, Bacillus licheniformis, Bacillus megaterium, Bacillus polymyxa*, and *Bacillus circulars*) and a mixture comprising the five bacterial strains, as described in Example 2.

The invention provides an optimised bacterial composition which proved safe, non-pathogenic when contacted with either intact or lacerated human body tissues, particularly effective in decomposing the organic pollutants that are present in the wastewater collection and transport pipes, and which can be applied to a biodegradable solid support, especially toilet paper, maintaining unaltered biodegradation activity upon storage for long periods of time and under disparate environmental conditions. The bacterial composition consists of five sporogenous strains of the genus *Bacillus*, which synergistically cooperate in the biodegradation of organic pollutants present in the wastewaters. The bacteria, or preferably their spores, are deposited on a biodegradable support and become active upon contact with water, thereby initiating the process of biological degradation of the organic pollutants. In particular, the activated bacteria produce enzymes that penetrate in depth into the organic agglomerates present in the wastewater pipes and/or collection tanks, promoting their decomposition into carbon dioxide and water. The bacteria mixture according to the invention has demonstrated a high synergistic biodegradation activity on wastewater from toilet pipes, also preventing the formation of large agglomerates which lead to blockages along sewer pipes and considerably reducing the organic pollutant content present in collection and processing tanks (trap tanks, septic tanks, Imhoff tanks, cesspools, seepage trenches etc.).

Accordingly, in a first embodiment the invention is directed to a product for the biodegradation of the organic substances contained in wastewaters from toilets, pipes and in sewage collection tanks, said product comprising a biodegradable solid support carrying a mixture of bacterial strains of the genus *Bacillus*, species *subtilis, licheniformis, megaterium, polymyxa* and *circulans*. The bacterial strains, preferably in the spore state, may be applied onto the biodegradable support in a liquid medium, preferably in form of solution or suspension in water optionally containing additives (e.g. stabilisers) and co-solvents. In a particularly preferred embodiment, the bacterial spores are used at a concentration of $10^6$ to $10^9$ CFU (colonies forming units) per ml. The bacterial mixtures have preferably the following quantitative composition: *B. subtilis* from 20 to 30%, *B. licheniformis* from 10 to 20%, *B. megaterium* from 10 to 20%, *B. polymyxa* from 20 to 30%, and *B. circulans* from 10 to 20%. Any bacterial strain of the indicated species may be used in accordance with the invention, irrespective of its origin or natural source.

The biodegradable support is preferably made of pure cellulose or of a cellulose derivative, e.g. recycled paper, de-inked paper, synthetic materials or non-woven fabrics; examples of cellulose or cellulose-derived products that can be used according to the invention include handkerchiefs, serviettes, napkins, diapers, sanitary towels, absorbing papers and preferably toilet paper. When the product is in form of toilet paper, a liquid culture of bacteria can be applied to at least one surface thereof by a process of spraying or coating, as described in further detail below. The same process can be used for other supports, if necessary with modifications depending on the shape, thickness, tensile strength, breakage resistance, loading capacity and other structural and mechanical characteristics of the support. Anyone skilled in the art will be able to determine the better conditions depending on the particular support and on the apparatus used for its manufacturing.

In addition to the bacteria, the biodegradable support may contain further ingredients including softening agents, surface-active agents, perfumes, dyes.

In a further embodiment, the invention relates to the use of a biodegradable solid support carrying the bacteria mixture described above, for degrading the organic substances contained in wastewaters and sewage, and for eliminating the organic agglomerates and the unpleasant odours that form in the wastewater pipes and collection tanks.

The following examples illustrate the invention in greater detail.

EXAMPLE 1

Preparation of the Bacterial Composition

The bacterial composition (hereafter indicated as B.A.T.P.L1700S) is an aqueous suspension of spores of the following bacterial strains:

Bacillus subtilis (ATCC 6051), Gram-positive, mesophilic, aerobic, produces endospores that are highly resistant even in environments which are not very favourable to biological growth, and produces a large variety of enzymes (protease and beta-glucanase) specific for sugars and starches.

Bacillus Licheniformis (ATCC 12713), Gram-positive, mesophilic, anaerobic, sporogenous, produces protease, amylase and lipase, specific for breaking down fats, resistant in environments with high concentrations of NaCl (up to 7%), denitrifying activity in anaerobic conditions, also grows at high temperatures (up to 50° C.).

Bacillus Megaterium (ATCC 14581), Gram-positive, mesophilic, aerobic, sporogenous, produces α,β-amylase enzymes specific for breaking down starches, protease for casein, resistant in environments with high concentrations of NaCl (up to 7%).

Bacillus Polymyxa (ATCC 842) Gram-positive, mesophilic, anaerobic, sporogenous, produces cellulase and hemicellulase specific for breaking down cellulose and paper, nitrifying activity.

Bacillus Circulans (ATCC 9500) Gram-positive, mesophilic, facultative anaerobic, sporogenous, produces protease, chitinase and pectinase, specific enzymes for breaking down plant derivatives, fibres and paper, resistant to high temperatures (up to 50° C.).

ATCC=American Type Culture Collection, Manassas, Va., USA

The biological product has the following characteristics:
APPEARANCE: cloudy liquid
COLOUR: straw yellow
pH: 8.2-8.8
DENSITY: 1000-1025 g/cm$^3$
STABILISER: propylene glycol
CFU/ml: $100 \times 10^7$
SAFETY: there is no risk, even in the event of improper use, such as swallowing, handling or contact, even with the genitals.

The bacteria count of 1 billion per g was specifically chosen to allow an appropriate application of product to each cm$^2$ of toilet paper; this count ensures a correct input of the bacterial pool into the sewers without damaging the toilet paper during manufacture of the roll.

The product is used in liquid form with or without added enzymes, perfumed, in aqueous emulsion or solvent.

EXAMPLE 2

Study of the Efficacy of the Individual Bacterial Strains in a Sewer System

The purpose of this study was to demonstrate that the biodegradation activity of the micro-organisms contained in the biological product B.A.T.P.L1700S is greater than that obtained by micro-organisms belonging to each type of bacterial strain taken separately. The test was conducted in a simulated sewer system by observing the variation in COD (Chemical Oxygen Demand) determined in a sample of water containing chemically oxidisable organic substances. The tests were conducted in parallel with a simulated sewer system with no biological treatment, subjected to the same experimental conditions.

The determination of the COD value in the wastewater provides a quantitative measurement of the presence of pollutant organic compounds. The reduction in COD caused by the micro-organisms is therefore a good indicator of the efficacy of the product used.

Procedure:

3.5 litres of water containing 3 g of sugar (source of carbon) and 3 g of nutrient compound (source of N.P.K.: 12:5:10) was prepared.

The solution was divided into seven 0.5 litre containers (A, B, etc.).

The COD of the solution was measured prior to treatment (after decanting for 1 h). The value found corresponds to the basal COD value for each sample.

The samples were kept under agitation (at very low speed) and at a constant temperature of 35° C. After agitation a sheet of toilet paper was added to each container.

Each sample was treated every day for 15 days as follows:

10 ml of water in container A 10 ml of Bacillus Subtilis $20 \times 10^6$ in container B 10 ml of Bacillus Licheniformis $20 \times 10^6$ in container C 10 ml of Bacillus Megaterium $20 \times 10^6$ in container D 10 ml of Bacillus Polymyxa $20 \times 10^6$ in container E 10 ml of Bacillus Circulans $20 \times 10^6$ in container F 1 ml of B.A.T.P.L1700S $1 \times 10^9$ in container G.

After treatment, each sample was subjected to agitation at very low speed for 10 min/day. Finally, a sheet of toilet paper was added.

The COD measurement and the treatment (T) were performed according to the following pattern:

| day | COD | T |
|---|---|---|
| 0 | | x |
| 1 | | x |
| 2 | | x |
| 3 | x | x |
| 4 | | x |
| 5 | | x |
| 6 | x | x |
| 7 | | x |
| 8 | | x |
| 9 | x | x |
| 10 | | x |
| 11 | | x |
| 12 | x | x |
| 13 | | x |
| 14 | | x |
| 15 | x | x |

The sample for COD determination was taken after leaving the solutions to stand for 1 h (without agitation). The sample was taken approx. 1 cm from the base of the container, taking care to avoid the solid component deposited and/or in suspension.

Results

TABLE a

COD values expressed in mg/litre

| day | A<br>water | B<br>subtilis | C<br>licheniformis | D<br>megaterium | E<br>polymyxa | F<br>circulans | G<br>BATPL1700S |
|---|---|---|---|---|---|---|---|
| 0 | 1850 | 1850 | 1850 | 1850 | 1850 | 1850 | 1850 |
| 3 | 1884 | 1721 | 2013 | 1699 | 1818 | 2005 | 1780 |
| 6 | 2405 | 1905 | 2288 | 2210 | 2153 | 2364 | 1106 |
| 9 | 3047 | 1899 | 2894 | 2573 | 2589 | 2792 | 884 |
| 12 | 3500(**) | 2157 | 2802 | 2781 | 2422 | 2807 | 653 |
| 15 | 3500(**) | 2100 | 2791 | 2664 | 2360 | 2640 | 488 |

(**)The maximum COD value detectable with the method used is 3500; for samples which fell outside this limit, the value of 3500 mg/L was conventionally indicated.

TABLE b

% reduction in pollutant content after treatment

| day | B<br>subtilis | C<br>licheniformis | D<br>megaterium | E<br>polymyxa | F<br>circulans | G<br>BATPL1700S |
|---|---|---|---|---|---|---|
| 0 | 0 | 0 | 0 | 0 | 0 | 0 |
| 3 | 9 | 0 | 10 | 4 | 0 | 6 |
| 6 | 12 | 5 | 8 | 10 | 2 | 54 |
| 9 | 10 | 5 | 6 | 15 | 8 | 71 |
| 12 | 18 | 13 | 15 | 14 | 14 | 81 |
| 15 | 25 | 15 | 10 | 15 | 13 | 86 |

Remarks

To demonstrate that biodegradation of the micro-organisms contained in B.A.T.P.L1700S is more effective than that of the individual bacterial strains, 7 identical simulated sewer systems with a known COD (basal value of 1850 mg/litre) were prepared.

A sheet of toilet paper was added to each sample for 15 consecutive days and the treatment described above under "procedure" was performed. The corresponding COD was measured every 3 days.

The percentage reductions in pollutant content for each treated sample compared with sample A (untreated=water) were calculated on the basis of the results obtained (Table a). The graph of FIG. 1 shows the total percentage reductions by the 5 strains (white bar) and the corresponding reduction by B.A.T.P.L1700S (grey bar). Table a) indicates that:

1) in a sewer system, in the absence of biological treatment (sample A), the COD tends to increase with time, ie. the concentration of chemically oxidisable organic substances (pollutants) increases.

2) in a sewer system, the presence of a biological treatment reduces the COD over time, ie. the concentration of chemically oxidisable organic substances (pollutants) is reduced by the degradation action of the micro-organisms. The different COD reduction percentages found, indicating different breakdown activities, are evidently dependent on the specificity of the enzymes produced by the bacteria. This specificity distinguishes each strain selected, and also depends on the more or less favourable environmental conditions of the sewer system. Under our conditions the most resistant strains, B. Subtilis and B. Polymyxa, demonstrated a more constant activity over time, which was superior in percentage terms to that of the other strains.

3) when treated with B.A.T.P.L1700S, the COD of the system decreases significantly over time due to the biodegradation activity of the micro-organisms belonging to all 5 strains contained in the product; in the presence of organic substances and favourable environmental conditions these micro-organisms become active, feed and reproduce, reducing the pollutant levels from 1850 on the first day to 488 on the last, namely a reduction of 86%.

The graph of FIG. 1 clearly shows that the biodegradation activity B.A.T.P.L1700S in the sewer system is superior to the sum of the activities of the 5 strains taken individually.

EXAMPLE 3

Study of the Efficacy of B.A.T.P.L1700S in a Sewer System

The purpose of this study was to establish the efficacy of biodegradation of the micro-organisms contained in B.A.T.P.L1700S in a simulated sewer system, by observing the variations in COD (Chemical Oxygen Demand) determined in a sample of water containing chemically oxidisable organic substances. This efficacy was compared with that of a product already on the market, namely WC Net Fosse Biologiche, a bacteria-based powder with a CFU count of 200 million per g, and compared with a system without biological treatment.

The determination of the COD value in the wastewater provides a quantitative measurement of the presence of pollutant organic compounds. The reduction in COD caused by the micro-organisms is therefore a good indicator of the efficacy of the product used.

Procedure:

1 litre of water containing 1 g of sugar (source of carbon) and 1 g of nutrient compound (source of N.P.K.: 12:5:10) was prepared.

The solution was divided between three 0.5 litre containers (A, B and C).

Prior to treatment, the COD of the solution was measured (after decanting for 1 h); the value found corresponds to the basal COD value for each sample.

The 3 samples were maintained under agitation (at a very low speed) and at a constant temperature of 35° C.

sample B: treated with 0.21 μL(*) of B.A.T.P.L1700S on ¼ sheet of toilet paper (approx. 25 $cm^2$).

Sample C: treated every 5 days with 5 ml of a solution consisting of 125 mg of WC Net in 500 ml, prepared according to the manufacturer's instructions.

1 sheet of paper with B.A.T.P.L1700S was inserted in sample B, and 1 sheet of untreated paper in sample A and sample C, every day for 15 consecutive days.

Sample A: treated every 5 days with 5 ml water.

After treatment, each sample was agitated at very low speed for 10 min/day.

The COD measurement, the addition of the toilet paper (F) and the treatment (T) were performed according to the following pattern:

| day | A = water | | | B = BATPL1700S | | | C = WC Net | | |
| --- | --- | --- | --- | --- | --- | --- | --- | --- | --- |
| | COD | F | T | COD | F | T | COD | F | T |
| 0 | | x | x | | x | x | | x | x |
| 1 | | x | | | x | x | | x | |
| 2 | | x | | | x | x | | x | |
| 3 | x | x | | x | x | x | x | x | |
| 4 | | x | | | x | x | | x | |
| 5 | | x | x | | x | x | | x | x |
| 6 | x | x | | x | x | x | x | x | |
| 7 | | x | | | x | x | | x | |
| 8 | | x | | | x | x | | x | |
| 9 | x | x | | x | x | x | x | x | |
| 10 | | x | x | | x | x | | x | x PHOTO |
| 11 | | x | | | x | x | | x | |
| 12 | x | x | | x | x | x | x | x | |
| 13 | | x | | | x | x | | x | |
| 14 | | x | | | x | x | | x | |
| 15 | x | x | x | x | x | x | x | x | x PHOTO |

The sample for the determination of COD was taken after leaving the solutions to stand for 1 h (without agitation); the sample was taken on the surface, at a depth of approx. 1 cm, avoiding the bacterial component and solids in suspension.

(*) dose equal to 5 g/60 m$^2$ of toilet paper

Results

TABLE c

| day | A = water | B = BATPL1700S | C = WC Net | |
| --- | --- | --- | --- | --- |
| 0 | 950 | 950 | 950 | |
| 3 | 1340 | 1280 | 2010 | |
| 6 | 1410 | 1390 | 1980 | |
| 9 | 3500 | 765 | 3027 | (**) |
| 12 | 2490 | 498 | 3500 | (**) |
| 15 | 2880 | 444 | 3108 | |

(**) The maximum COD value obtainable with the method used is 3500; for samples exceeding this limit, the value of 3500 mg/l was conventionally indicated.

Remarks

To demonstrate the efficacy of biodegradation of the microorganisms contained in B.A.T.P.L1700S and compare it with that of a known product, 3 identical simulated sewer systems with a known COD were prepared.

A sheet of toilet paper was added to each sample for 15 consecutive days: untreated for samples A and C, treated with B.A.T.P.L1700S for sample B, as described under "Procedure". Samples A and C were treated every 5 days with water and "WC Net Fosse Biologiche" respectively at the dose stated above. The corresponding COD was measured every 3 days.

Figure 2:
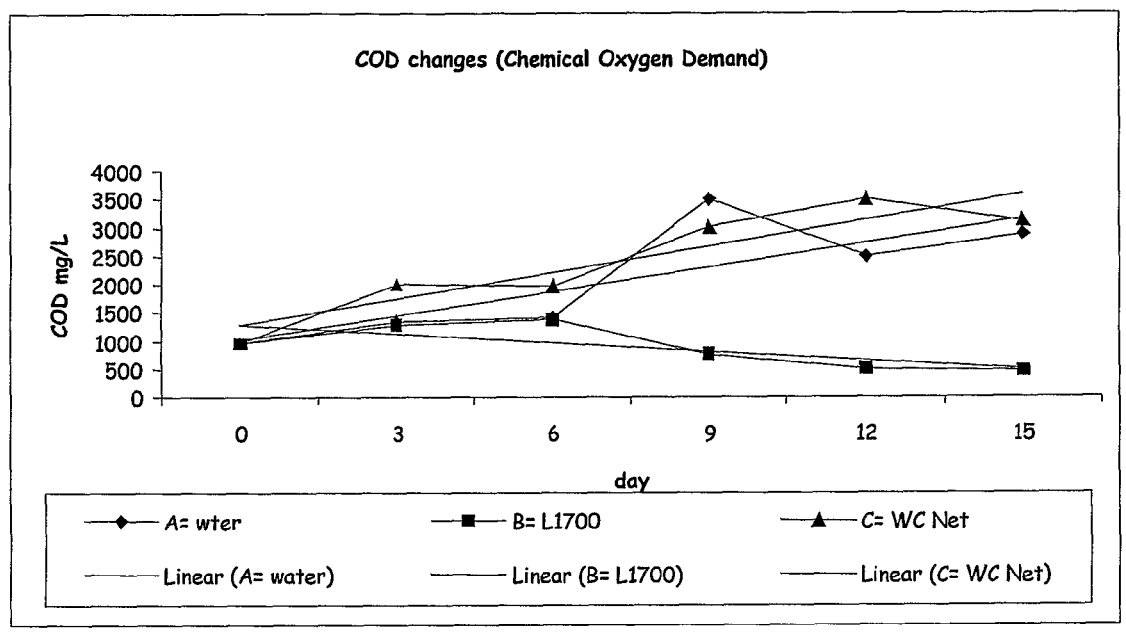
FIG. 2 is a graph demonstrating the efficacy of biodegradation of B.A.T.P.L1700S and WC Net Fosse Biologiche, as described in Example 3.

The results obtained were recorded on the graph of FIG. 2; the line that statistically interpolates all the values obtained ("trend line"), was calculated for each set of data corresponding to each sample. The graph indicates that:

1) In a sewer system, in the absence of biological treatment (sample A), the COD tends to increase with time, ie. the concentration of chemically oxidisable organic substances (pollutants) increases.

2) The treatment performed with "WC Net Fosse Biologiche" proved ineffective; paradoxically, a trend line of higher COD values was observed in sample A.

3) In the case of treatment with B.A.T.P.L1700S, the COD of the system declined over time due to the biodegradation activity of the micro-organisms contained in the product; in the presence of organic substances and favourable environmental conditions these micro-organisms become active, feed and reproduce, reducing the pollutant levels.

Macroscopic observation of the 3 samples with the naked eye also confirmed the results of the COD measurement.

Figure 3:
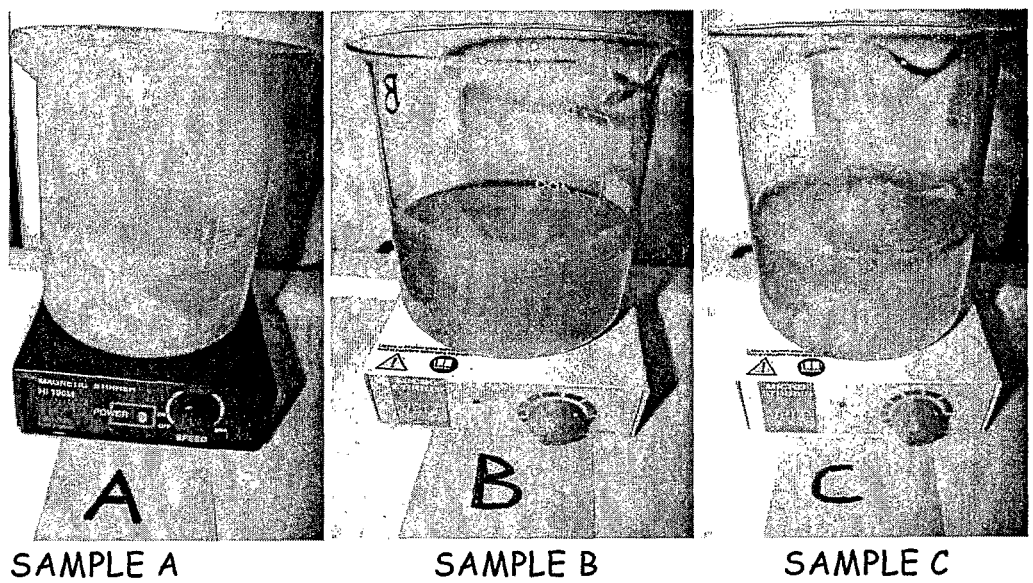
FIG. 3 is a macroscopic photograph of the samples on the tenth day, as described in Example 3.

Each sample was photographed on the 10th day (FIG. 3).

Sample A: cloudy supernatant liquid with particulate matter deposited on the base and intact sheets of paper still clearly evident and not decomposed.

Sample B: supernatant liquid clearer than in A, homogenous particulate matter deposited on the base, paper is decomposed.

Sample C: cloudy liquid, floating particulate part containing the sheets of intact paper, still clearly evident, and mould formation.

Figure 4:
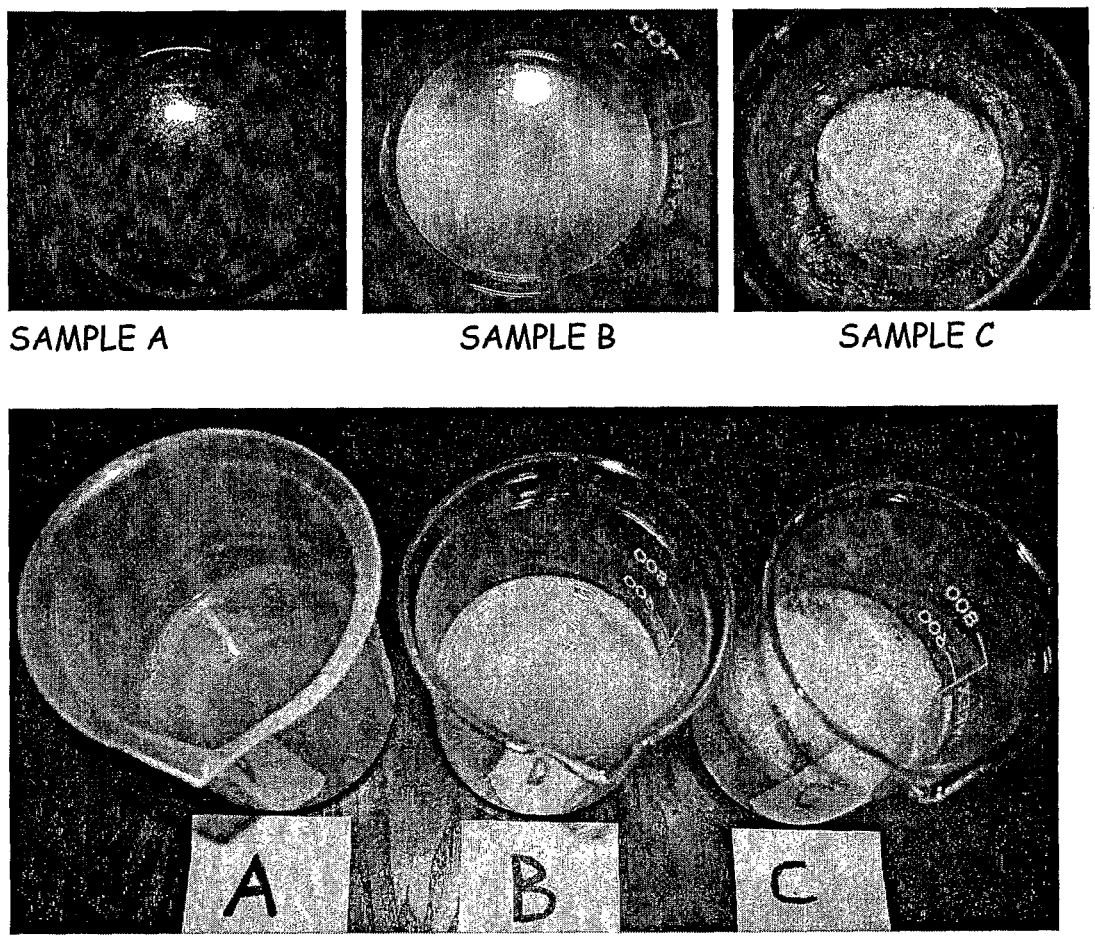
FIG. 4 is a macroscopic photograph of the samples on the fifteenth day, as descrbied in Example 3.

Photos taken on the 15th day (FIG. 4):

Sample A: Supernatant liquid cloudy, large deposits on the base and toilet paper still clearly distinguishable, mould formation.

Sample B: Homogenous supernatant liquid, toilet paper broken down and dissolved, thick but homogenous deposits on the base, no formation of mould and/or Sample C: supernatant liquid cloudy, large deposits on the base and toilet paper still clearly distinguishable, mould formation.

EXAMPLE 4

Evaluation of the Optimum cfu/(Cm$^2$ of Paper) Ratio

Domestic Use

On the assumption that the average weekly consumption of toilet paper by a family of four is approx. 5 rolls, and that each roll is approx. 19 m long and 10 cm wide, approx. 9.5 m$^2$ (1900 cm×10 cm×5 rolls=95000 cm$^2$) of toilet paper a week is discharged into the sewers.

The correct load of bacterial strains into the sewer pipes of such a family has been calculated at 2,000 million CFU/week to activate and maintain the process of decomposition of the organic substances, eliminate unpleasant odours and fully dissolve the cellulose particles.

The amount obtained, namely 2,000 million CFU, equal to 2 g of the B.A.T.P.L1700S product, must be deposited on 9.5 m$^2$ of toilet paper.

Use in Communities

On the assumption that the average weekly toilet paper consumption of a hotel with 20 double rooms, namely 40 guests, is approx. 40 rolls, and that each roll is approx. 19 m long and 10 cm wide, approx. 76 m$^2$ (190 cm×10 cm×40 rolls=760000 cm$^2$) of toilet paper a week is discharged into the sewers.

The correct load of bacterial strains into the sewer pipes of such a hotel has been calculated at 25,000 million CFU/week to activate and maintain the process of decomposition of the organic substances, eliminate unpleasant odours and fully dissolve the cellulose particles.

The amount obtained, namely 25,000 million CFU, equal to 25 g of the B.A.T.P.L1700S product invented, must be deposited on 76 m² of toilet paper.

EXAMPLE 5

Application of Bacteria to Paper

The product can be applied to toilet paper by two methods: spraying or coating.

The spraying apparatus can be installed in the converting unit (where the finished paper is bonded, cut and packaged) or the final part of the paper mill, where the finished paper is rewound and sent to the converting unit for subsequent processing.

The spraying application in the converting unit takes place at the "paper passage point" before "embossing and gluing", "DESL" or "tip-to-tip", depending on the type of processing selected. The plant is situated immediately before the sheet bonding process.

In the paper mill the apparatus is positioned at the point preceding the sheet bonding stage and after the roll rewinding stage, called the "big roll" stage.

The spray application system comprises nozzles that spray (according to the speed of the machine) a quantity of product sufficient to cover the entire length of the final roll.

The nozzles operate by collision of 2 converging jets, one of compressed air and the other of bacterial product, to a create a jet consisting of particles with an average diameter of under 10 microns. The system includes a storage tank for the bacterial product under agitation, a feed pump, 1-5 atomiser nozzles, depending on the aperture and speed of the machine (converting unit or rewinder), a screen that conveys the jet into the two layers, management software, and a system that controls the quantity delivered on the basis of the number of machine revolutions (acceleration or slowing of the speed of the machine).

If the spray method is used, our biological product can be combined with the dose of softener following a biocompatibility test.

In the coating application system (the rotogravure type of flexographic system) the product is taken up by a "honeycomb" steel roller with microperforations which passes over a subsequent roller, and distributes the bacterial product on the paper. This type of application can be used in the converting unit at the final stage in the paper mill, or at the place where the paper is rewound.

If the coating (flexographic) method is used, the bacteria can be combined with the sheet-bonding adhesive, following a biocompatibility test.

The invention claimed is:

1. A product for the biodegradation of organic substances contained in the wastewaters from toilets, pipes and in sewage collection tanks, which comprises a biodegradable solid support carrying a synergistically effective mixture of bacterial strains consisting of *Bacillus subtilis, Bacillus licheniformis, Bacillus megaterium, Bacillus polymyxa* and *Bacillus circulans*, wherein said product is non-pathogenic when used on human body tissues, wherein the biodegradable solid support comprises recycled paper, de-inked paper, synthetic materials, and/or non-woven fabrics, and is selected from the group consisting of handkerchiefs, serviettes, napkins, diapers, sanitary towels, absorbing papers, and toilet paper.

2. The product according to claim 1, wherein the bacterial strains are spores.

3. The product according to claim 1, wherein the biodegradable solid support contains softening agents, surface-active agents, perfumes and/or dyes.

4. The product according to claim 1, wherein the toilet paper comprises the mixture of bacterial strains on more than one surface.

5. A process for the manufacturing of the product of claim 1, comprising spraying or coating the biodegradable solid support with a synergistically effective mixture of bacterial strains consisting of *Bacillus subtilis, Bacillus licheniformis, Bacillus megaterium, Bacillus polymyxa* and *Bacillus circulans*.

6. The process according to claim 5, wherein the mixture of bacterial strains are in the form of a solution or suspension in water optionally containing additives and co-solvents.

7. The process according to claim 6, wherein the concentration of the mixture of bacterial strains ranges from $10^6$ to $10^9$ colony-forming units (CFU) per ml.

8. A method for degrading organic substances contained in wastewaters from toilets, pipes, and in sewage collection tanks and for reducing organic agglomerates and unpleasant odours that form in wastewater pipes and collection tanks, comprising providing the product of claim 1 in a wastewater pipe or collection tank.

\* \* \* \* \*